United States Patent [19]

Klemm

[11] Patent Number: Plant 7,018

[45] Date of Patent: Sep. 5, 1989

[54] GERANIUM NAMED MARKONI

[75] Inventor: Siegfried Klemm, Stuttgart, Fed. Rep. of Germany

[73] Assignee: Klemm & Sohn, Stuttgart, Fed. Rep. of Germany

[21] Appl. No.: 244,921

[22] Filed: Sep. 15, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new variety of geranium plant particularly distinguished by its profuse production of flowers having a nice, somewhat brick red color, the individual florets having the form of a cup with six to nine imbricated petals, and about sixty-five of these florets together forming a delicate cluster which stands on a flower stem of about 17 cm. long and extending upwardly from a strong, upright stalk of about 23 to 25 cm. in length. The foliage of this plant is well formed and contains a moderate amount of green leaves that are of medium to small size, the foliage body standing about 20 cm. above the soil. This new plant is an early blooming variety resistant to heat and rain, as well as to botrytis, and for these reasons, seems to be an ideal variety for mass production for the general market.

1 Drawing Sheet

BACKGROUND OF THE NEW PLANT

This new geranium plant originated as a seedling of a hybrid resulting from my crossing in 1985 of unnamed plants, growing in my nursery at Stuttgart, West Germany, with the primary object of seed collection. This particular seedling was selected for propagation because of its attractive flower coloration, its profuse production of flowers, and its early blooming habit. Propagation of this particular seedling by means of cuttings from the parent plant was done by me and under my direction at Stuttgart with very satisfactory results and such propagation was carried on at Stuttgart through several successive generations, which demonstrated clearly that the novel and advantageous characteristics of the new plant were fully retained from generation to generation and appeared to be firmly fixed, thus assuring its homogeneity.

DESCRIPTION OF THE DRAWING

This new geranium plant is illustrated by the accompanying full color photographic drawing, which shows the flower form, bud clusters in several stages of development, and the character of the foliage of this plant, the color shown being as true to that herein specified as is reasonably possible to obtain by conventional, professional photographic procedures.

DESCRIPTION OF THE NEW PLANT

The following is a detailed description of my new geranium cultivar based upon observation made in the Fall of 1987 of plants of this variety grown in greenhouse, as well as outdoors, the color designations being according to The R.H.S. Colour Chart published by The Royal Horticultural Society of London, England.

THE PLANT

Origin: Seedling.
Parentage: Unknown.
Classification:
- *Botanic.*—*Pelargonium zonale* hybrid.
- *Commercial.*—Geranium.

Form: Round and bushy.
Height: About 40 cm.
Growth: Upright and spreading with good strength and a medium growth rate.
Branching character: Normal.
Flower stem length: About 17 cm.
Foliage:
- *Quantity.*—Moderate.
- *Leaf size.*—Small.
- *Leaf shape.*—Orbiculate with crenate margin.
- *Texture.*—Smooth.
- *Ribs and veins.*—Five or six main veins on each leaf.
- *Color.*—Upper side — Medium Green. Under side — Light Green.

THE BUD

Size: Medium.
- *Diameter.*—About 12 mm.
- *Length.*—About 12 to 15 mm.

Shape: Generally elliptical.
Rate of opening: Medium.
Color of florets:
- *When sepals first divide.*—Very Light Pink.
- *When petals begin to unfurl.*—Pink to Red.

Sepals:
- *Number.*—Five.
- *Shape.*—Linear.
- *Character.*—The sepals stand up as the flowers open.
- *Color.*—Green.

Calyx:
- *Shape.*—There is nearly no calyx and what appears is broad in size.
- *Splitting.*—There is no splitting.
- *Aspect.*—Smooth.

Flower stem:
- *Length.*—About 17 cm.
- *Character.*—Erect and rigid.
- *Color.*—Green.

THE INFLORESCENCE

Blooming habit: Continuous and profusely from early Spring to late Fall.

Clusters:

*Size.*—Medium.

*Shape.*—Generally round.

*Number of florets.*—About sixty-five.

*Stalk.*—Length: About 23 to 25 cm. Character: Strong and upright.

Florets:

*Size.*—Medium. Diameter — About 5 cm. Depth — About 1 cm.

*Borne.*—Singly on the umbel stem of a cluster.

*Shape.*—When bloom first opens, cup-shaped. When bloom matures, flat cup.

*Petalage.*—Number of petals: Six to nine. Arrangement: Imbricated. Form: Obovate with entire margins. Texture: Soft. Color: Dutch Vermilion, R.H.S. 40-A.

Petaloids:

*Number.*—One to three.

*Size.*—About 4 to 7 mm.

*Color.*—Brick Red.

Flower stem:

*Length.*—About 17 cm.

*Color.*—Green.

*Character.*—Upright and strong.

Discoloration after full bloom: None.

Effect of weather: Very little.

Persistence: Old flowers fall down.

Disease resistance: Resistance to botrytis as observed in the wet weather of 1987 in the region of Stuttgart, West Germany.

Lasting quality: Normal.

THE REPRODUCTIVE ORGANS

Stamens:

*Number.*—Seven.

*Arrangement.*—In a ring around the ovary.

*Anthers.*—Size: About 1.5 mm. Color: Dark Orange.

*Filaments.*—Length: About 4.5 mm. Color: White.

*Pollen.*—Color: Orange.

Pistil:

*Number.*—One.

*Style.*—Length: About 5 mm. Color: White Green.

*Stigma.*—Five parts. Color: Pink Frosted Glas.

Character of ovaries: Normal.

THE FRUIT

Fertility: The fruit is fertile.

Shape: Ovoid.

Color at maturity: Dark Brown.

This new geranium cultivar is very floriferous and being registant against heat, rain and botrytis, it is an ideal variety for the mass market.

I claim:

1. The new and distinctive geranium cultivar and the parts thereof, substantially as herein shown and described, particularly distinguished by its early blooming habit and profuse production of Dutch Vermilion flowers.

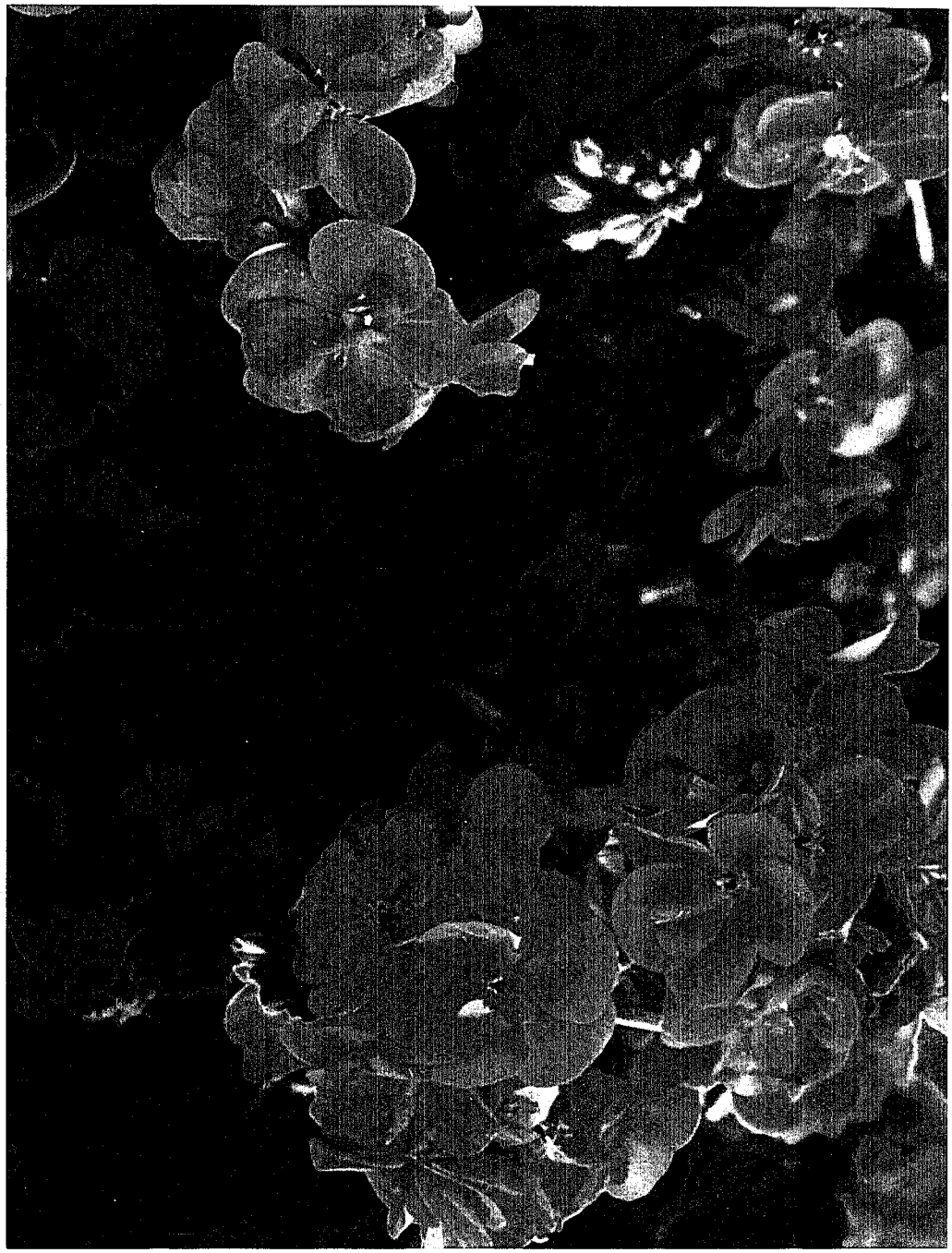

* * * * *